United States Patent
Teles et al.

(10) Patent No.: US 6,673,950 B1
(45) Date of Patent: Jan. 6, 2004

(54) METHOD FOR REACTING AN ORGANIC COMPOUND WITH A HYDROPEROXIDE

(75) Inventors: Joaquim Henrique Teles, Altrip (DE); Alwin Rehfinger, Mutterstadt (DE); Peter Bassler, Viernheim (DE); Norbert Rieber, Mannheim (DE); Anne Wenzel, Eggenstein-Leopoldshafen (DE); Andreas Walch, Schwaigern (DE); Wolfgang Harder, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 259 days.

(21) Appl. No.: 10/030,183

(22) PCT Filed: Jul. 31, 2000

(86) PCT No.: PCT/EP00/07383

§ 371 (c)(1),
(2), (4) Date: Feb. 1, 2002

(87) PCT Pub. No.: WO01/10855

PCT Pub. Date: Feb. 15, 2001

(30) Foreign Application Priority Data

Aug. 4, 1999 (DE) ......................................... 199 36 547

(51) Int. Cl.⁷ ..................... C07D 301/19; C07D 301/12
(52) U.S. Cl. .................... 549/529; 549/530; 549/531
(58) Field of Search .............................. 549/529, 530, 549/531

(56) References Cited

U.S. PATENT DOCUMENTS

| 5,481,012 A | 1/1996 | Caubere et al. ............. 549/531 |
| 6,380,119 B1 | 4/2002 | Grosch et al. ................ 502/49 |

FOREIGN PATENT DOCUMENTS

| DE | 19723949 A1 | 12/1998 |
| DE | 99 01445 | 1/1999 |
| EP | 0 230 949 | 8/1987 |
| EP | 0 434 546 | 6/1991 |
| EP | 0 712 852 | 5/1996 |
| EP | 0 757 043 | 2/1997 |
| EP | 0 930 308 | 7/1999 |
| WO | 98/55228 | 12/1998 |

OTHER PUBLICATIONS

M.G. Clerici et al.: "Epoxidation of lower olefins with hydrogen peroxide and titanium silicalite" Journal of Catalysis, vol. 140, No. 1, pp. 71–83, Mar. 1, 1993.

M.G. Clerici, et al.: "Synthesis of propylene oxide from propylene and hydrogen peroxide catalyzed by titanium silicalite" Journal of Catalysis, vol. 129, pp. 159–167, 1991.

*Primary Examiner*—Ba K. Trinh
(74) *Attorney, Agent, or Firm*—Oblon, Spivak, McClelland, Maier & Neustadt, P.C.

(57) ABSTRACT

In a process for reacting an organic compound with a hydroperoxide using at least one heterogeneous catalyst, both the pH and the temperate of the reaction medium are changed during the reaction

20 Claims, 1 Drawing Sheet

METHOD FOR REACTING AN ORGANIC COMPOUND WITH A HYDROPEROXIDE

This application is a 371 of PCT/EP00/07383, dated Jul. 31, 2000.

The present invention relates to a process for reacting an organic compound with a hydroperoxide using a heterogeneous catalyst wherein both the pH and the temperature of the reaction medium are changed during the reaction. In a further embodiment, the present invention relates to a process in which the pressure under which the reaction occurs is changed in addition to the pH and the temperature of the reaction medium.

In reactions of organic compounds with a hydroperoxide in the presence of a heterogeneous catalyst, the activity of the heterogeneous catalyst generally decreases on prolonged use.

To be able to reuse the catalyst, it is in these cases necessary to remove the catalyst from the reactors in which the reactions are carried out and regenerate it outside the reactors. In the case of heterogeneous titanium silicalite catalysts which are used, for example, for the reaction of olefins with hydroperoxide solutions, such regeneration processes are carried out, for example, by calcination of the catalyst at elevated temperature, as described, for example, in J. Catal. 129 (1991) 159–166. Another possibility, which is likewise described in this publication, is to wash the catalyst with suitable solvents. Since regeneration by these methods can only be carried out after the catalyst has been removed from the reactor, these processes are complicated and therefore undesirable from the point of view of process economics. Further regeneration methods are described, for example, in WO 98/55228 and the prior art cited therein.

To counter the gradual deactivation of heterogeneous catalysts which are used in the reaction of organic compounds with a hydroperoxide, it is also possible to regulate the temperature during the reaction so as to compensate for the deactivation. It is likewise conceivable for temperature and pressure to be changed during the reaction in order to compensate for the deactivation of the catalysts. This method is described, for example, in WO 99/01445, where temperature and pressure are simultaneously increased during the reaction of propene with an active oxygen species in the liquid phase over a heterogeneous catalyst.

A further possible way of influencing the selectivity of, for example, titanium silicalites is described in J. Catal. 140 (1993) 71–83. It is found there that, without quantitative results being reported, the addition of alkali metal hydroxides in the epoxidation of lower olefins in low concentrations increases the yield, but does not influence the selectivity. However, at relatively high base concentrations, the activity of the titanium silicalite may be completely suppressed. The epoxidation of allyl chloride, which is described in the same document, is significantly impaired by the addition of neutral salts such as LiCl when using a titanium silicalite, while the addition of HCl improved the activity of the catalyst. In contrast, the addition of the neutral salt LiCl in the epoxidation of 1-butene does not adversely affect the activity of the catalyst.

EP-A 0 712 852 discloses the use of a nonbasic salt to improve the selectivity of a titanium silicalite catalyst which is used for the epoxidation of olefinic compounds by means of hydrogen peroxide. The experiments were carried out in the batch mode at constant temperatures.

EP-B 0 230 949 discloses a process for the epoxidation of olefinic compounds by means of hydrogen peroxide, in which the selectivity of the catalysts used, viz. synthetic zeolites, can be significantly improved by adding, either before or during the reaction, compounds which neutralize the acid groups on the catalyst surface. The process described was carried out under isothermal conditions.

P-A 0 757 043 describes a process for preparing epoxides from olefins and hydrogen peroxide in the presence of a titanium-containing zeolite as catalyst, in which neutral or acidic salts are added to the catalyst before or during the reaction. The temperatures in the reaction of the olefins with hydrogen peroxide were kept constant.

It is found in practice that the deactivation of the catalyst often does not occur uniformly. Rather, the initial activity, which is generally very high, decreases very quickly. This is followed by a relatively slow deactivation which can extend over some hundreds of hours.

It is an object of the present invention to provide a process which allows a flexible response to these different deactivation rates of heterogeneous catalysts which occur in reactions of organic compounds with hydroperoxides.

Figure 1:
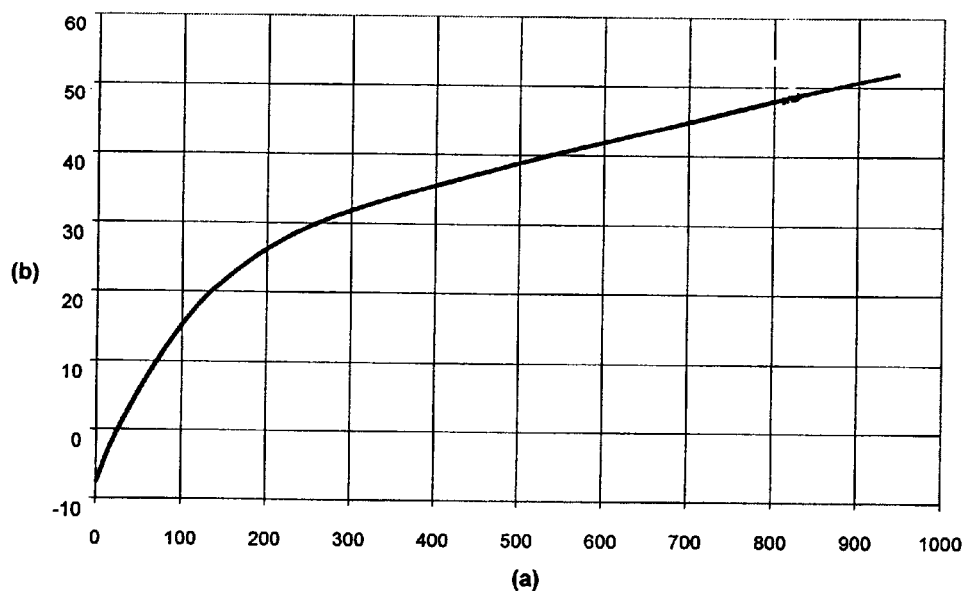
FIG. 1 shows thermostat temperature as a function of time.

We have found that this object is achieved by a process for reacting an organic compound with a hydroperoxide using at least one heterogeneous catalyst, wherein both the pH and the temperature of the reaction medium are changed during the reaction.

As far as the way in which the process is carried out is concerned, all conceivable embodiments are possible. In particular, the reaction can be carried out either in the batch mode or continuously. Of course, mixed forms are also conceivable, for example when the reaction is carried out in two or more stages. In this case, it is conceivable for the reaction in at least one stage to be carried out batchwise and the reaction in at least one further stage to be carried out continuously.

In a preferred embodiment, the reaction of the hydroperoxide with the organic compound is carried out continuously, with, in particular, a continuous stream of hydroperoxide being fed into the reaction medium in which the reaction takes place.

Accordingly, the present invention also provides a process as described above in which a hydroperoxide solution is added continuously to the reaction medium.

It is of course also conceivable for two or more different hydroperoxide solutions which may, for example, differ in hydroperoxide concentration, pH or temperature to be added to the reaction medium.

The pH of the reaction medium, which in the process of the present invention is changed during the reaction of the hydroperoxide with the organic compound, can be changed by all conceivable means.

Thus, for example, it is conceivable to add at least one acidic compound or at least one basic compound or a mixture of two or more thereof directly to the reaction medium. The acidic or basic compound or the mixture of two or more thereof may be dissolved in a suitable solvent or solvent mixture before it is added to the reaction medium and the solution can then be added to the reaction medium. Both the addition of the acidic or basic compound or the mixture of two or more thereof and the addition of the solution can be carried out continuously or discontinuously, and it is also conceivable, for example, for two or more identical or different compounds or mixtures or solutions to be added separately from one another, with the additions being able to be carried out continuously or discontinuously.

The pH of the reaction medium can of course also be changed via the feed streams which flow continuously into the reaction medium during the process. Thus, it is conceivable for the pH of a solvent stream or a feed stream comprising the organic compound or else a feed stream comprising both solvent and organic compound to be changed prior to addition to the reaction medium and for the pH of the reaction medium to be influenced in this way.

In a preferred embodiment of the process of the present invention, the pH of the reaction medium is changed during the reaction by altering the pH of the hydroperoxide solution which is added continuously to the reaction medium.

The present invention therefore also provides a process as described above in which the change in the pH of the reaction medium is achieved by changing the pH of the hydroperoxide solution which is added to the reaction medium.

The control of the pH by means of the hydroperoxide stream can in principle be carried out by all conceivable methods.

For example, it is conceivable for a hydroperoxide stream which is added to the reaction medium to be divided into two or more substreams before the addition and the pH of at least one substream to be brought to a desired value. The two or more substreams can subsequently be combined again and fed into the reaction medium as a single combined stream. It is likewise conceivable for the substreams to be fed into the reaction medium separately from one another or, in the case of more than two substreams, in any appropriate combination. The pH of the reaction medium can be set either by changing the pH of at least one substream or by appropriate metering of amounts of substreams or by a combination of these methods.

Furthermore, it is likewise conceivable to vary the pH of the reaction medium by cometering of hydroperoxide solution and at least one suitable basic compound or at least one acidic compound or a mixture of two or more thereof or as described above, if desired a solution of at least one of these compounds in a suitable solvent. In such a case, hydroperoxide solution and the acidic or basic compound or compounds or a solution thereof can be combined in appropriate proportions before the addition to the reaction medium. It is likewise conceivable for the hydroperoxide solution and the acidic or basic compound or compounds or a solution thereof to be introduced as separate, appropriately metered streams into the reaction medium.

The reaction of the organic compound with hydroperoxide can in principle be carried out in one or more steps. In particular, it is conceivable for the organic compound to be reacted with hydroperoxide in a first step, unreacted hydroperoxide to be separated off from the mixture obtained as a result of the reaction and, in a second step which is carried out in a different reactor from that in which the first reaction is carried out, the hydroperoxide which has been separated off to be reacted once again with the organic compound.

The present invention therefore also provides a process as described above which comprises at least the steps (i) to (iii):

(i) reacting the hydroperoxide with the organic compound to give a mixture comprising the reacted organic compound and unreacted hydroperoxide, (ii) separating the unreacted hydroperoxide from the mixture resulting from step (i), (iii) reacting the hydroperoxide which has been separated off in step (ii) with the organic compound, where the reactions in steps (i) and (iii) are carried out in at least two separe reactors and both the pH and the temperature of the reaction medium are changed in at least one of the reactors used in steps (i) and (iii).

In the process of the present invention, the hydroperoxide can be separated off in the abovementioned separation step (ii) by all customary methods known from the prior art. Should a plurality of separation steps (ii) be provided, it is also possible for different separation methods to be used in different separation steps.

The hydroperoxide is preferably separated off by distillation in the separation step. Depending on the requirements of the process, it can be separated off in one or more distillation columns. Preference is given to using one distillation column in the separation step for separating off the hydroperoxide.

In the process of the present invention, it is possible for not only the hydroperoxide but also the reacted organic compound to be separated off in one separation apparatus from the mixture resulting from the first reaction step (i) in which the organic compound is reacted with the hydroperoxide. It is naturally also possible for the reaction product remaining after the hydroperoxide has been separated off to be transferred to a further separation apparatus specifically provided for this purpose and the reacted organic compound to be separated from the reaction there.

In both cases, it is possible, for example, to collect the reacted organic compound in the separation apparatuses and separate it off after the reactions of the organic compound with the hydroperoxide are complete.

However, the reacted organic compound is preferably separated off in addition to the hydroperoxide in the respective separation apparatus. If the separation is carried out by distillatior, it is possible, for example, to take off the reacted organic compound at the top and to separate the hydroperoxide from the mixture as a side offtake.

When a distillation unit is used as separation apparatus in the process of the present invention, it is naturally likewise possible to separate off the hydroperoxide from the mixture not via a side off take but at the bottom.

If the hydroperoxide and/or the reacted organic compound are/is taken off in a distillation unit, it is possible, in the process of the present invention, for any high-boiling components of the mixture which are formed as by-products from the reaction of the organic compound with the hydroperoxide to be separated off at the bottom. It is also conceivable to reduce the temperature at the bottom by, for example, addition of preferably gaseous, low-boiling components, e.g. the organic compound itself, preferably propene.

Examples of such low-boiling components are hydrocarbons having from 1 to 4 carbon atoms, for example methane, ethane, propane, butane, ethene or butenes. It is likewise possible to use, for example, nitrogen or argon.

Of course, it is also possible to react a plurality of organic compounds with the hydroperoxide in the process of the present invention.

If a plurality of organic compounds are reacted with the hydroperoxide in step (i), various products resulting from the reactions can be present in the mixtures. If these are in turn separated off by distillation in the separation step (i), it may be necessary to provide a plurality of distillation columns for the separation.

The separation in step (ii) is preferably carried out so that a liquid mixture comprising the hydroperoxide is separated off. It is possible for the hydroperoxide-containing mixture which has been separated off to further comprise, in addition to the hydroperoxide, for example small amounts of unreacted organic compound and/or reacted organic compound. Likewise, solvents may be present in the mixture comprising the hydroperoxide which has been separated off.

If the reacted organic compound is also separated off in the separation apparatus in step (i), then this separation, from which a liquid mixture or a liquid/gas mixture is preferably obtained, results in a stream which comprises the reacted organic compound and possibly the unreacted organic compound and/or small amounts of solvents.

After the steps (i) and (ii) have been carried out in the process of the present invention, the hydroperoxide which has been separated off is reacted once again with the organic compound in step (iii) in a reactor which is different from the reactor used in step (i).

As reactors, it is of course possible to use all conceivable reactors which are best suited to the respective reactions. In the process of the present invention, a reactor is not restricted to a single vessel. Rather, it is also possible to use a cascade of stirred vessels, for example as reactor which is used in step (i) or (ii).

The reactors used in the process of the present invention are preferably fixed-bed reactors. Further preference is given to fixed-bed tube reactors as fixed-bed reactors.

As hydroperoxides to be used in the process of the present invention, it is possible to employ all hydroperoxides which are known from the prior art and are suitable for the reaction of the organic compound.

Examples of such hydroperoxides are t-butyl hydroperoxide and ethylbenzene hydroperoxide, which can be prepared from isobutane and oxygen or ethylbenzene and oxygen.

As hydroperoxide solution, preference is given to using a hydrogen peroxide solution, in particular an aqueous hydrogen peroxide solution, in the present process.

To prepare hydrogen peroxide, recourse can be made, for example, to the anthraquinone process which is used to produce virtually all the world production of hydrogen peroxide. This process is based on the catalytic hydrogenation of an anthraquinone compound to form the corresponding anthrahydroquinone compound, subsequent reaction of this with oxygen to form hydrogen peroxide and subsequent separation of the resulting hydrogen peroxide from the reaction mixture by extraction. The catalysis cycle is closed by the anthraquinone compound which has been obtained back being hydrogenated again.

An overview of the anthraquinone process is given in "Ullmann's Encyclopedia of Industrial Chemistry", 5th Edition, Volume 13, pages 447 to 456.

It is likewise conceivable to obtain hydrogen peroxide by conversion of sulfuric acid into peroxodisulfuric acid by anodic oxidation accompanied by simultaneous evolution of hydrogen at the cathode. The peroxodisulfuric acid is then hydrolyzed to form firstly peroxosulfuric acid and subsequently hydrogen peroxide and sulfuric acid, which is thus recovered.

It is of course also possible to prepare hydrogen peroxide from the elements.

The pH of the hydroperoxide solution, in particular the hydrogen peroxide solution, can in principle be adjusted by all customary methods. Care merely has to be taken to ensure that the addition of acidic or basic compounds or addition of a solution comprising acidic or basic compounds to the hydroperoxide solution does not have an adverse effect on the subsequent reaction of the organic compound with hydroperoxide and the pH does not go outside the stability range of the hydroperoxide used.

Accordingly, the present invention also provides a process as described above in which the pH of the hydroperoxide solution is changed
(a) by treatment of the hydroperoxide solution with at least one ion exchanger or
(b) by addition of
   (aa) an acidic compound or
   (bb) a basic compound or
   (cc) a neutral compound or
   (dd) a mixture of two or more thereof to the hydroperoxide solution or
(c) by a combination of methods (a) and (b).

It is in principle possible to use both strongly basic and weakly basic compounds or both strongly acidic and weakly acidic compounds. In particular, the following salts are conceivable:

Ammonium salts, alkali metal salts, especially lithium, sodium and potassium salts, and alkaline earth metal salts. The anions of these salts include, for example, halides such as chloride and bromide, nitrate, sulfate and hydroxide and also the anions of phosphorus-, arsenic- antimony- and tin-containing acids, e.g. perchlorate, phosphate, hydrogenphosphate, dihydrogenphosphate, arsenate and stannate. Other anions such as formate, acetate, hydrogencarbonate or carbonate are also conceivable. Examples of salts are lithium chloride, lithium bromide, sodium bromide, lithium nitrate, sodium nitrate, potassium nitrate, lithium sulfate, sodium sulfate, potassium sulfate, sodium hydroxide, potassium hydroxide, ammonium hydroxide, sodium carbonate, sodium hydrogencarbonate, potassium carbonate, lithium carbonate, potassium hydrogencarbonate, lithium hydrogencarbonate and potassium hydrogenphosphate and also lithium acetate, magnesium acetate, calcium acetate, barium acetate or ammonium acetate. Mention may also be made of carboxylates derived from carboxylic acids, in particular carboxylic acids having from 1 to 10 carbon atoms, and also alkoxides derived from alcohols having from 1 to 10 carbon atoms. Further examples include ammonium dihydrogenphosphate, sodium dihydrogenphosphate, potassium dihydrogenphosphate, disodium dihydrogenpyrophosphate, tetrasodium pyrophosphate.

As solvent for the basic or acidic compounds, preference is given to using an aqueous solvent mixture, particularly preferably a mixture with the solvent used in the reaction, e.g. methanol.

As described above, it is also possible to set the pH of the hydroperoxide solution by treatment of the hydroperoxide solution with at least one ion exchanger. In the process of the present invention, it is in principle possible to use cation exchangers and anion exchangers.

If only one type of ion exchanger is used, use of at least one anion exchanger is preferred. If a plurality of ion exchangers are used, they can be used simultaneously or in succession.

For the purposes of the present invention, it is in principle possible to use all ion exchangers known to those skilled in the art, for example organic ion exchangers such as those based on polystyrene, or inorganic ion exchangers such as hydrotalcites and other sheet silicates which may contain exchangeable carbonate, hydrogencarbonate or hydroxide groups.

Examples of basic ion exchangers which are particularly preferred for the purposes of the present invention are polystyrene resins containing tertiary amine groups, for instance the commercially available anion exchangers Lewatit® MP62 and Lewatit® MP 63 and also Dowex® MWA/1 and Dowex® AMW-500. The use of polystyrene resins containing, for example, quaternary ammonium groups and having hydroxide counterions is also conceivable. Examples of such resins are the commercially available ion exchangers Lewatit® OC-1950 and also Dowex® 1, Dowex® 2, Dowex® 11, Dowex® 21K and Dowex® 550A.

In the preferred embodiment of the process of the present invention, which comprises steps (i) and (iii), it is possible to adjust the pH of the hydroperoxide solution with which the organic compound is reacted in step (i) and also the pH of the hydroperoxide solution which is separated off in step (ii). Thus, it is possible to change either the pH of the reaction medium in the reactor of step (i) or the pH of the reaction medium in the reactor of step (iii) or the pH of both reaction media during the reaction of hydroperoxide with the organic compound.

Conceivable heterogeneous catalysts are in principle all catalysts which are suitable for the respective reaction. Preference is given to using catalysts which comprise a porous oxidic material such as a zeolite. Particular preference is given to using catalysts which comprise a titanium-, vanadium-, chromium-, niobium- or zirconium-containing zeolite as porous oxidic material.

As is known, zeolites are crystalline aluminosilicates having ordered channel and cage structures and pore openings in the micropore range below 0.9 nm. The network of such zeolites is made up of $SiO_4^-$ and $AlO_4^-$ tetrahedra which are joined by common oxygen bridges. An overview of the known structures may be found, for example, in M. W. Meier, D. H. Olson, Ch. Baerlocher, "Atlas of Zeolite Structure Types", 4th Edition, Elsevier, London, 1996.

To balance the negative charge resulting from incorporation of Al(III) into the Si(IV) silicate lattice, zeolites contain exchangeable cations, in particular cations of sodium, potassium, lithium or cesium, depending on the method of preparation. If these cations are replaced by protons, for example by ion exchange, the corresponding acidic solid having a zeolite structure, known as the H form, is obtained.

Zeolites which do not contain any aluminum and in which the Si(IV) in the silicate lattice is partly replaced by titanium as Ti(IV) are also known. These titanium zeolites, in particular those having a crystal structure of the MFI type, and possible ways of preparing them are described, for example, in EP-A 0 311 983 and EP-A 405 978. Apart from silicon and titanium, such materials may further comprise additional elements such as aluminum, zirconium, tin, iron, cobalt, nickel, gallium, boron or small amounts of fluorine. In the zeolite catalysts used in the process of the present invention, some or all of the titanium of the zeolite can be replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites having an MFI structure can, as is known, be identified by a particular X-ray diffraction pattern and also by means of a lattice vibration in the infrared region (IR) at about 960 $cm^{-1}$.

Preference is given to using Ti, Ge, Te, V, Cr, Nb, Zr zeolites, in particular Ti zeolites.

Specific examples are Ti Ge, Te, V, Cr, Nb or Zr zeolites of the structral types ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG, ZON and ITQ-4 or mixed structures derived from two or more of these structures or mixtures of two or more thereof, with particular preference being given to those having an MFI structure, a BEA structure, an MEL structure, an ITQ-4 structure or an MFI/MEL mixed structure. Zeolites of this type are described, for example, in the abovementioned reference by W. M. Meier et al.

Particularly preferred catalysts are the Ti-containing zeolite catalysts generally known as "TS-1", "TS-2", "TS-3", "ZSM-48" and "ZMS-12", in each case with Ti, TTM-1, Ti-RUT, titanium-containig zeolites of the types "UTD-1", "CIT-5", CIT-1" and "SSZ-24" and also Ti zeolites having a lattice structure isomorphous with beta-zeolite.

For example, titanium zeolites as are known from, for example, U.S. Pat. No. 3,329,481 are used. In such titanium zeolites, part of the Si(IV) originally present in the silicate lattice is replaced by titanium as Ti(IV). Further titanium zeolites, in particular those having a crystal structure of the MFI type, and also possible ways of preparing them are described, for example, in U.S. Pat. No. 4,410,501, EP-A 0 311 983, U.S. Pat. No. 4,666,692, DE-A 3 047 798 or BE 1 001 038, which are hereby fully incorporated by reference into the present application Further titanium-containing zeolites which can readily be used for the purposes of the present invention and have a structure different from the MFI structure are descnbed, for example, in EP-A 0 405 978. Apart from silicon and titanium, such zeolites can further comprise additional elements such as aluminum (described, for example, in DE-A 31 41 283), gallium (EP-A 0 266 825), boron (U.S. Pat. No. 4,666,692) or small amounts of fluorine (EP-A 0 292 363). The disclosures relating to zeolites in the abovementioned documents are hereby also filly incorporated by reference into the present application.

Further zeolite catalysts which can be used in the process of the present invention are described, for example, in U.S. Pat. No. 5,430,000 and WO 94/29408, whose relevant contents are hereby incorporated by reference into the present application.

Further titanium-contaiing zeolites which may be mentioned are those having the ferrierite or β-zeolite structure or the mordenite structure.

In addition, the following zeolite catalysts can be used in the process of the present invention:

Catalysts having a zeolite structure as described in DE-A 196 23 611.8, whose contents relating to the catalysts are hereby fully incorporated by reference into the present application.

These are oxidation catalysts based on titanium silicates or vanadium silicates having a zeolite structure, with preferred zeolite structures being as listed above. These catalysts are shaped by consolidating shaping processes, as described in detail in the above patent application.

Furthermore, it is possible to use oxidation catalysts based on titanium silicates or vanadium silicates having a zeolite structure and containing from 0.01 to 30% by weight of one or more noble metals selected from the group consisting of ruthenium, rhodium, palladium, osmium, iridium, platinum, rhenium, gold and silver, which catalysts have likewise been shaped by consolidating shaping processes. Such catalysts are described in DE-A 196 23 609.6, the contents of which relating to the catalysts are hereby fully incorporated by reference into the present application.

As regards the consolidating shaping processes, the binders and the auxiliaries and the structure of the oxidation catalysts, DE-A 196 23 611.8 is hereby incorporated by reference.

The oxidation catalyst described in DE-A 196 23 609.6 contains from 0.01 to 30% by weight, in particular from 0.05 to 15% by weight, especially from 0.1 to 8% by weight, in each case based on the amount of the titanium or vanadium zeolites, of the specified noble metals. Particular preference is given to palladium. The noble metals can be applied to the catalyst in the form of suitable noble metal components, for example in the form of water-soluble salts, before, during or after the consolidating shaping step.

Furthermore, it is possible to use the following catalysts for the purposes of the present invention:

A shaped body which comprises at least one porous oxidic material and is obtainable by a process which comprises the following steps:

(I) admixing a mixture comprising a porous oxidic material or a mixture of two or more thereof with a mixture comprising at least one alcohol and water, and (II) kneading, shaping, drying and calcining the mixture obtained from step (I).

Details regarding this catalyst may be found in DE-A 197 23 751.7, which is hereby fully incorporated by reference into the present application.

According to the present invention, it is also possible to use solids which compose silicon dioxide and can be prepared by a process which comprises the following step (I):

(I) Bringing at least one precursor of silicon dioxide into contact with at least one structure former in a liquid medium, wherein the structure former is a polyethylenimine or a mixture of two or more thereof.

Details regarding this solid may be found in DE-A 197 32 865.2, whose relevant contents are hereby fully incorporated by reference into the present application.

Further catalysts which can readily be used are shaped bodies which comprise an inert support and at least one silicate, preferably a crystalline silicate, applied thereto and are obtainable by applying a mixture comprising at least one silicate and at least one metalic acid ester or a hydrolysate thereof or a combination of metalic acid esters and hydrolysate thereof to an inert support, as are described in DE-A 197 54 924.1 whose relevant contents are likewise incorporated by reference into the present application.

Furthermore, it is possible, according to the present invention, to use shaped bodies which comprise at least one silicate and at least one metal oxide and can be prepared by a process which comprises the following step (i):

(i) mixing the silicate or silicates with at least one metal oxide sol which has a low content of alkali metal ions and alkaline earth metal ions, as described in DE-A 198 15 879.3.

The relevant contents of that patent application are likewise incorporated by reference into the present application.

According to the present invention, it is also possible to use titanium silicalites which have an RUT structure and can be prepared by a process which comprises steps (i) and (ii):

(i) preparation of a mixture of at least one $SiO_2$ source and at least one titanium source;

(ii) crystallization of the mixture from (i) in a pressure vessel with addition of at least one template compound to give a suspension, wherein template compounds used are amines or ammonium salts which are suitable for stabilizing cages of the silicate structure $[4^45^46^2]$ and $[4^45^66^58^1]$.

Details regarding these catalysts may be found in DE-A 198 39 792.5.

Furthermore, it is possible, according to the present invention, to use the silicon dioxides containing mesopores and micropores as described in DE-A 198 47 630.2, which preferably have one or more of the following features (i) to (iii):

(i) a sun of the specific surface areas of the mesopores and micropores of at least 300 $m^2/g$;

(ii) a sum of the pore volumes of the mesopores and micropores of at least 0.2 ml/g;

(iii) a maximum of the pore diameter distribution of the mesopores at at least 3 nm.

Further details regarding these catalysts may be found in the abovementioned application, whose relevant contents are fully incorporated by reference into the present application.

The present invention therefore also provides a process as described above in which the heterogeneous catalyst comprises a titanium-containing zeolite.

Furthermore, the present invention also provides a process as described above in which the titanium containing zeolite is a TS-1 zeolite.

As reactions which are possible in the process of the present invention, mention may be made by way of example of the following:

the epoxidation of olefins, e.g. the preparation of propene oxide from propene and $H_2O_2$ or from propene and mixtures which supply $H_2O_2$ in situ;

hydroxylations such as the hydroxylation of monocyclic, bicyclic or polycyclic aromatics to form monosubstituted, disubtituted or more highly substituted hydroxyaromatics, for example the reaction of phenol and $H_2O_2$ or of phenol and mixtures which supply $H_2O_2$ in situ, to produce hydroquinone;

oxime formation from ketones in the presence of $H_2O_2$ or mixtures which supply $H_2O_2$ in situ and ammonia (ammonoximation), for example the preparation of cyclohexanone oxime from cyclohexanone;

the Baeyer-Villiger oxidation.

In the process of the present invention, preference is given to using organic compounds which have at least one C—C double bond.

As examples of such organic compounds having at least one C—C double bond, mention may be made of the following alkenes:

ethene, propene, 1-butene, 2-butene, isobutene, butadiene, pentenes, piperylene, isoprene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprene, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils. In the process of the present invention, preference is given to using alkenes which contain from 2 to 8 carbon atoms. Particular preference is given to reacting ethene, propene and butene. Very particular preference is given to reacting propene.

Accordingly, the present invention also provides a process in which the organic compound is propene.

As regards the alteration of the temperature of the reaction medium in which the reaction of the hydroperoxide with the organic compound takes place, essentially all conceivable methods are possible. For example, the temperature of the reaction medium can be controlled via the temperature of at least one feed stream which is preferably introduced into the reaction medium in continuous operation.

The temperature is preferably varied by means of suitable thermostatting of the reactor or reactors. Here too, it is possible to employ all suitable methods. For example, the reactor or reactors can be provided with a double wall through which, for example, there is passed a liquid by means of whose temperature the temperature of the reaction medium in the reactor is set. It is of course also conceivable to provide various zones of the reactor or reactors with separate double walls and to pass, for example, liquids having differing temperatures around the various zones. The setting of different temperatures in different zones is of course not restricted to arrangements in which the reactor is provided with one or more double walls, but can also be achieved by means of all other suitable methods.

It is likewise conceivable, for example, to introduce two or more hydroperoxide streams having different pH values into various zones of the reactor or reactors in order, for example, to set pH values which differ from zone to zone in the reaction medium.

It is naturally also conceivable both to set different temperatures in various zones of the reactor or reactors and to set different pH values of the reaction medium in these zones.

For the purposes of the present invention, it is in principle possible to vary temperature and pH separately from one another during the reaction of the hydroperoxide with the organic compound. Thus, for example, it is conceivable to vary the pH in one step, to vary the temperature in a next step and to vary the pH again in a next step. Of course, it is also conceivable to vary the pH in one step and to vary the temperature in both the next steps. Quite generally, the variation of pH and temperature can be carried out in all suitable and conceivable steps. Furthermore, it is of course possible to change pH and temperature simultaneously. These parameters are preferably changed continuously, more preferably simultaneously and continuously.

pH and temperature are preferably changed in such a way that a constant activity of the heterogeneous catalyst is achieved. This is generally achieved by increasing the temperature of the reaction medium with the running time. Depending on the type of catalyst used, it is possible to counter deactivation of the catalyst by increasing or decreasing the pH of the reaction medium. If, in a preferred embodiment of the process of the present invention, a titanium-containing silicalite is used as heterogeneous catalyst, the pH is generally reduced during the course of the reaction.

The present invention therefore also provides a process as described above in which the pH of the reaction medium is reduced during the reaction.

It is of course conceivable for one or more temperature reductions or one or more pH increases to be carried out during the reaction in order, for example, to match the activity and selectivity of the catalyst to a desired value.

A particular advantage of the process of the present invention is that when the pH of the reaction medium is varied appropriately, significantly smaller temperature changes are necessary than would be the case if the pH were not changed.

At a reaction pressure of 30 bar, the temperatures set in the process of the present invention are generally in the range from 0 to 120° C., preferably in the range from 10 to 90° C. and more preferably in the range from 20 to 70° C. The pH of the reaction medium is generally in the range from 2 to 6 and particularly preferably in the range from 3 to 6. In long-term operation, the temperatures are preferably changed by 2° C./day or less, more preferably by from 0.2 to 1.0° C./day, and the pH is preferably changed by 0.5/day or less, more preferably by from 0.01 to 0.2/day.

In addition to the parameters temperature and pH of the reaction medium, the pressure under which the reaction takes place can also be varied in the process of the present invention. It is possible for, in one or more steps, the pressure and pH to be varied while the temperature is kept constant or the pressure and temperature to be varied while the pH is kept constant, as long as the pH and the temperature of the reaction medium are varied over the total duration of the reaction.

As far as the variation of the pressure is concerned, recourse can be made, in the process of the present invention, to all methods which are known from the prior art or are otherwise suitable. However, preference is given to working at pressures under which no gas phase is present.

In the process of the present invention, the heterogeneous catalyst can naturally be pretreated by all suitable methods before use. Pretreatment of heterogeneous titanium silicalite catalysts is described, for example, in the abovementioned EP-B 0 230 949, whose relevant contents are hereby incorporated by reference into the present application.

It is likewise conceivable for the catalyst to be regenerated by means of all suitable methods after the reaction. Such regeneration methods are described, for example, in the abovementioned J. Catal. 129 (1991), pp. 159–166, and WO 98/55228, whose relevant contents are hereby incorporated by reference into the present application.

The following examples illustrate the process of the present invention.

EXAMPLES

Example 1

Comparative Example

A tube reactor which had a diameter of 24 mm and a length of 2000 mm and was provided with a double wall was charged with 565 g of catalyst. The catalyst was a TS-1 catalyst and was used in the form of shaped bodies having a diameter of 2 mm. It was prepared as described in WO 97/31711, whose relevant contents are incorporated by reference into the present application.

The reactor was then flooded with methanol, the reaction pressure was set to 30 bar and the introduction of methanol at a rate of 1560 g/h was commenced. The jacket space of the reactor was connected to a thermostat to regulate the temperature and the initial temperature was set to −5° C.

The following starting materials were then metered in from pressure reservoirs by means of HPLC pumps:

134 g/h of propene, 99.5% pure,
214 g/h of hydrogen peroxide, aqueous, concentration= 50%, pH=2.

The product leaving the reactor was depressurized and analyzed. The conversion was determined by titration of the unreacted hydrogen peroxide with titanyl sulfate. The selectivity was determined by means of gas chromatography. During the experiment, the temperature set at the thermostat was changed so that the hydrogen peroxide conversion at the outlet from the reactor remained constant at 85±3%. The propylene oxide selectivity as a proportion of the hydrogen peroxide reacted remained essentially constant during the entire experiment and was in the range from 92 to 95%.

The thermostat temperature as a function of time is shown in FIG. 1.

In the figure:
(a) denotes time/h
(b) denotes thermostat temperature/°C.

Example 2
Continuous Epoxidation of Propylene with Matching of Temperature and pH to Activity of Ion Exchangers The reaction was carried out in a manner analogous to example 1 with the following alterations: instead of one hydrogen peroxide solution, two hydrogen peroxide solutions having different pH values were metered in. An aqueous 50% strength hydrogen peroxide solution having a pH of 6 was introduced via the first metering unit, while an aqueous 50% strength hydrogen peroxide solution having a pH of 2 was introduced via the second metering unit. The hydrogen peroxide solution having the pH of 6 was prepared by treatment of the commercial product with a basic ion exchanger (e.g. Serdolit® Blue from Boehringer, Ingelheim, or Amberlite® IRA-68 from Rohm & Haas) at 0° C.

The pH of the streams was regulated by means of a glass electrode and they were metered in using a ratio regulator in such a way that any desired pH in the range from 2 to 6 could be set.

The hydrogen peroxide solution which had been set to the desired pH was then fed into the reactor as in example 1. As initial conditions, a temperature of 25° C. and a pH of 6.0 was set The product leaving the reactor was then depressurized and analyzed. The conversion was determined by titration of the unreacted hydrogen peroxide with titanyl sulfate. The selectivity was determined by means of gas chromatography. During the experiment, the temperature set at the thermostat was increased at a constant rate of 0.2° C./day and the pH of the hydrogen peroxide solution fed in was reduced so that the hydrogen peroxide conversion at the reactor outlet remained constant at 85±3%. The propylene oxide selectivity based on the hydrogen peroxide reacted remained within the range from 92 to 95% during the entire experiment.

Figure 2:
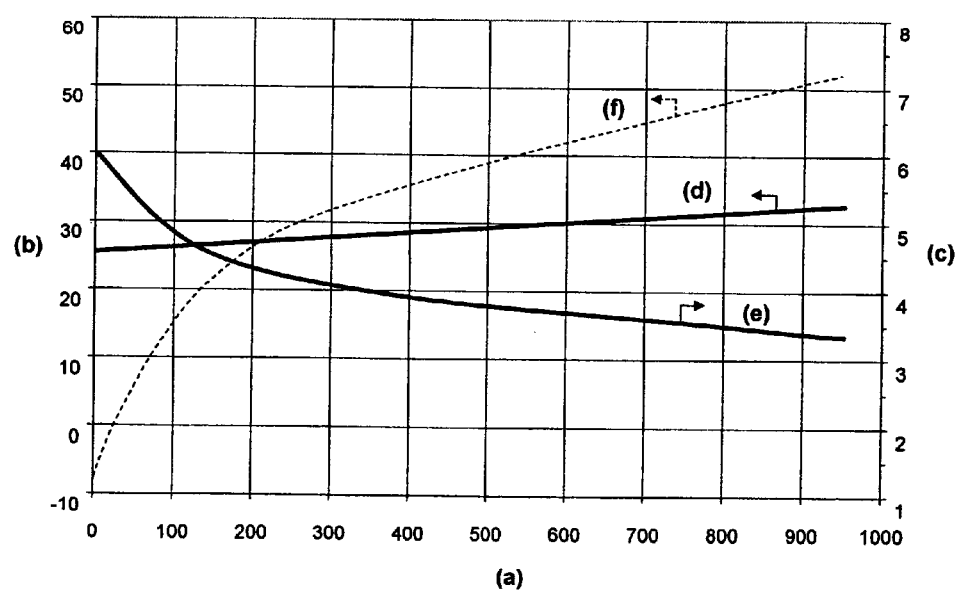
FIG. 2 shows thermostat temperature and pH of the hydrogen peroxide solution as a function of time.

The thermostat temperature and the pH of the hydrogen peroxide solution used are shown as functions of time in FIG. 2. The temperature curve from example 1 is drawn in as a broken line for comparison.

In FIG. 2:
(a) denotes time/h
(b) denotes thermostat temperature/°C.
(c) denotes pH
(d) denotes temperature curve
(e) denotes pH curve
(f) denotes temperature curve from example 1

The experiment was stopped after 950 hours. As can be seen from FIG. 2, the temperature range required and the required rate of change of temperature could be significantly reduced by simultaneously changing temper and pH.

We claim:

1. A process for reacting an organic compound with a hydroperoxide, said process comprising
   reacting said organic compound and said hydroperoxide in the presence of at least one heterogeneous catalyst, wherein both the pH and the temperature of a reaction medium are changed during the reaction.

2. The process as claimed in claim 1, wherein the hydroperoxide is added continuously to the reaction medium.

3. The process as claimed in claim 2, wherein a change in the pH of the reaction medium is achieved by changing the pH of the hydroperoxide which is added to the reaction medium.

4. The process as claimed in 1, further comprising at least the steps (i) to (iii):
   (i) reacting the hydroperoxide with the organic compound to give a mixture comprising a reacted organic compound and an unreacted hydroperoxide,
   (ii) separating said unreacted hydroperoxide from said mixture resulting from step (i),
   (iii) reacting said unreacted hydroperoxide which has been separated off in step (ii) with the organic compound,
   wherein steps (i) and (iii) are carried out in at least two separate reactors and both the pH and the temperature of the reaction medium are changed in at least one of the reactors used in steps (i) and (iii).

5. The process as claimed in claim 2, further comprising at least the steps (i) to (iii):
   (i) reacting the hydroperoxide with the organic compound to give a mixture comprising a reacted organic compound and an unreacted hydroperoxide,
   (ii) separating said unreacted hydroperoxide from said mixture resulting from step (i),
   (iii) reacting said unreacted hydroperoxide which has been separated off in step (ii) with the organic compound,
   wherein steps (i) and (iii) are carried out in at least two separate reactors and both the pH and the temperature of the reaction medium are changed in at least one of the reactors used in steps (i) and (iii).

6. The process as claimed in claim 3, further comprising at least the steps (i) to (iii):
   (i) reacting the hydroperoxide with the organic compound to give a mixture comprising a reacted organic compound and an unreacted hydroperoxide,
   (ii) separating said unreacted hydroperoxide from said mixture resulting from step (i),
   (iii) reacting said unreacted hydroperoxide which has been separated off in step (ii) with the organic compound,
   wherein steps (i) and (iii) are carried out in at least two separate reactors and both the pH and the temperature of the reaction medium are changed in at least one of the reactors used in steps (i) and (iii).

7. The process as claimed in claim 4, wherein the pH of the hydroperoxide is changed
   (a) by treating the hydroperoxide with at least one ion exchanger or
   (b) by adding an acidic salt, a basic salt, a neutral compound, or a mixture of two or more thereof to the hydroperoxide, or
   (c) by a combination of (a) and (b).

8. The process as claimed in claim 2, wherein the hydroperoxide is an aqueous hydrogen peroxide solution.

9. A process as claimed in claim 1, wherein the heterogeneous catalyst comprises a titanium-containing zeolite.

10. The process as claimed in claim 1, wherein the organic compound contains at least one C—C double bond.

11. The process as claimed in claim 1, wherein the pH of the reaction medium is reduced during the reaction.

12. The process as claimed in claim 1, wherein the pressure is changed.

13. The process as claimed in claim 2, wherein the pressure is changed.

14. The process as claimed in claim 3, wherein the pressure is changed.

15. The process as claimed in claim 4, wherein the pressure is changed.

16. The process as claimed in claim 5, wherein the pressure is changed.

17. The process as claimed in claim 6, wherein the pressure is changed.

18. The process as claimed in claim 7, wherein the pressure is changed.

19. The process as claimed in claim 9, wherein the pressure is changed.

20. The process as claimed in claim 10, wherein the pressure is changed.

* * * * *